United States Patent [19]

Schroeder et al.

[11] Patent Number: 4,888,325

[45] Date of Patent: Dec. 19, 1989

[54] CONTROLLING PLANT PESTS WITH COMPOSITIONS CONTAINING ALKYL GLYCOSIDE

[75] Inventors: Peter Schroeder, Viersen; Hans Bouten, Geldern; Manfred Biermann, Muelheim, all of Fed. Rep. of Germany

[73] Assignee: Henkel Kommanditgesellschaft auf Aktien, Duesseldorf, Fed. Rep. of Germany

[21] Appl. No.: 945,923

[22] Filed: Dec. 23, 1986

[30] Foreign Application Priority Data

Dec. 23, 1985 [DE] Fed. Rep. of Germany ....... 3545908

[51] Int. Cl.$^4$ .............................................. A01N 43/16
[52] U.S. Cl. ..................... 514/25; 536/1.1; 536/4.1; 536/18.3; 424/405; 47/DIG. 11
[58] Field of Search .................. 536/1.1, 4.1, 18.3; 424/405; 47/DIG. 11; 514/25

[56] References Cited

U.S. PATENT DOCUMENTS

| | | | |
|---|---|---|---|
| 3,157,964 | 11/1964 | Ferguson et al. | 47/DIG. 11 |
| 3,547,828 | 12/1970 | Mansfield et al. | 252/351 |
| 3,598,865 | 8/1971 | Lew | 536/18.6 |
| 3,707,535 | 12/1986 | Lew | 536/18.6 |
| 3,772,269 | 11/1973 | Lew | 536/18.6 |
| 3,839,318 | 10/1974 | Mansfield | 536/18.6 |
| 3,983,214 | 9/1976 | Misato et al. | 514/23 |
| 4,335,236 | 6/1982 | Tsuyumu et al. | 536/18 |
| 4,349,669 | 9/1982 | Klahr et al. | 536/127 |
| 4,556,505 | 12/1985 | Fenn | 47/DIG. 11 |
| 4,561,995 | 12/1985 | Fenn | 47/DIG. 11 |
| 4,681,617 | 7/1987 | Ghyczy et al. | 47/DIG. 11 |

FOREIGN PATENT DOCUMENTS

| | | |
|---|---|---|
| 0077167 | of 0000 | European Pat. Off. |
| 2302685 | 10/1976 | France |
| 54-40145 | 3/1979 | Japan ............................ 47/DIG. 11 |
| 55-88633 | 7/1980 | Japan ............................ 47/DIG. 11 |
| 61-212231 | 9/1986 | Japan ............................ 47/DIG. 11 |
| 2166974 | 5/1986 | United Kingdom |

OTHER PUBLICATIONS

CA 90:82069z.
CPI 85:156869.

Primary Examiner—Ronald W. Griffin
Assistant Examiner—Nancy S. Carson
Attorney, Agent, or Firm—Ernie G. Szoke; Wayne C. Jaeschke; Real J. Grandmaison

[57] ABSTRACT

A method for treating plants to control plant pests by applying to the locus of the pests an alkyl glycoside or an alkyl glycoside and an additional plant pest-control agent.

18 Claims, No Drawings

CONTROLLING PLANT PESTS WITH COMPOSITIONS CONTAINING ALKYL GLYCOSIDE

BACKGROUND OF THE INVENTION

1. Field of the Invention

The present invention relates to the use of long chain ethers in compositons to protect plants from harmful organisms, such as insects, mites, and fungi.

2. Statement of Related Art

At the present time, useful and ornamental plants are protected against pests, disease and weeds by various methods from the purely mechanical removal of weeds and pests to controlled changes in the plant germ-plasm. However, the most common method is still the use of chemical control agents because, in this way, success can generally be obtained more simply and more quickly than with other methods.

However, the use of chemical agents often involves the disadvantage of unwanted side effects which may be attributed, for example, to high toxicity or inadequate degradability, and—in the case of pests—the development of resistance, often after only a short time. Today, the need to overcome these disadvantages is almost as much an incentive in the search for new agents as the desire to find stronger and more selective agents.

The desire to find agents having a favorable spectrum of properties was also the starting point of the developments which culminated in the present invention.

DESCRIPTION OF THE INVENTION

Other than in the operating examples, or where otherwise indicated, all numbers expressing quantities of ingredients or reaction conditions used herein are to be understood as modified in all instances by the term "about".

The present invention is based on the discovery that certain long-chain alkyl glycosides, some of which have been known as surfactants, also show advantageous properties in the field of plant protection.

Accordingly, the present invention relates to compositions containing at least one alkyl glycoside corresponding to the following general formula

$$H(\text{-glyc})_n\text{-R}x(EO)_m \qquad (I)$$

in which (-glyc) represents the residue of a monosaccharide, n is a number of from 1 to 6, R is a primary $C_8$–$C_{22}$ alkyl or alkenyl group attached by a glycoside bond to the (-glyc) group, EO is the ethyleneoxy group and m is a number of from 0 to 100; and to the use of such compositions as agents for controlling harmful organisms in preparations for the protection of useful and ornamental plants.

These alkyl glycosides are distinguished by an unusually broad action spectrum against harmful organisms and are unexpectedly capable of supplementing or enhancing the effect of a number of known plant protection agents and herbicides. The effect of the alkyl glycosides in this regard is quite different from that of other surfactants of the type normally used as auxiliaries, for example as emulsifiers or spreading agents, in the application of agricultural chemicals.

The alkyl glycosides used in the practice of the invention exhibit fungicidal, insecticidal, and acaricidal activity and, by virtue of these properties, can be used as the sole active substance in the pest control compositions. In this particular form of application, the low toxicity and the good biodegradation of the compounds are particularly advantageous, especially since there is also generally no need to add organic solvents or emulsifiers. Accordingly, preparations based on these alkyl glycosides are also particularly suitable for application to plants intended for consumption either wholly or in part, even in cases where they are shortly to be harvested.

However, the alkyl glycosides can also be used in combination with other active substances such as insecticides, fungicides, virucides, acaracides, herbicides, growth regulators, ripening accelerators, repellents, leaf fertilizers, and others. They are preferably used in combination with other insecticides, fungicides, acaricides, and/or herbicides. In combinations with insecticides, fungicides, or acaricides, not only can the individual effects be added together, a synergistic enhancement of the insecticidal, fungicidal, or acaricidal effect is also obtained. The use of the alkyl glycosides in combination with other insecticides, fungicides and acaricides has the further advantage of counteracting any development of resistance in plant pests. In this case, too, the alkyl glycosides are preferably used in combination with active substances which, like the alkyl glycosides, are not toxic to warm-blooded animals or which are very rapidly converted into harmless products, particularly for preparations which are to be used on food plants.

Earlier published German Patent Application Nos. 34 41 587.4-41 and P 35 07 380.2-41 describe the use of alkyl glycosides as wax emulsifiers in evaporation-inhibiting additives which are intended for use in agriculture. This use is not the subject of the present application.

The alkyl glycosides used in the practice of the present invention can be prepared by known methods. In this connection, reference is made to U.S. Pat. Nos. 3,547,828; 3,707,535; 3,839,318; 3,598,865; 3,547,828; 3,772,269; and 4,349,669; and to European Patent Application 77,167.

One synthesis of commerical significance comprises the acid-catalyzed condensation of monosaccharides of the aldose type corresponding to the formula H(-glyc)H with long-chain primary alcohols of the formula (R—OH) containing from 8 to 22 and preferably from 8 to 18 carbon atoms. Alkyl glycosides corresponding to the following formula

$$H(\text{glyc})_n\text{-R} \qquad (II)$$

in which the value of n may be varied within wide limits through the choice of the reaction conditions, are formed with elimination of water. Alkyl glycosides corresponding to formulae I and II, in which n=1 to 6, are suitable for use in accordance with the invention, although it is preferred to use compounds in which n=1 to 3. In products where the value of n is greater than 1, n represents a statistical mean value. The alkyl glycosides corresponding to formula I are obtained from the compound of formula II by addition of ethylene oxide, preferably in the presence of alkaline catalysts, for example, in accordance with U.S. Pat. Nos. 2,407,002. Alkyl glycosides containing from 0 to 10 moles of ethylene oxide are preferred, alkyl glycosides completely free from ethylene oxide being particularly preferred.

The alkyl glycosides can also be prepared from oligo- or polysaccharides which, in the course of the acid-catalyzed reaction, are first depolymerized by hydrolysis and/or alcoholysis to lower fragments before the alkyl glycosides corresponding to formula II are formed. Mixtures of different reducing monosaccharides or polysaccharides containing various monosaccharide units may also be used as starting materials, in which case alkyl glycoside molecules of correspondingly mixed composition may be formed where the value of n is greater than 1.

The following monosaccharides are suitable as starting materials: glycose, mannose, galactose, arabinose, apiose, lyxose, gallose, altrose, idose, ribose, xylose and talose and the oligo- and polysaccharides composed of these monosaccharides, for example maltose, lactose, maltotriose, hemicellulose, starch, partial hydrolyzates of starch, and sugar syrup.

However, alkyl glycosides made up of the same monosaccharide units are preferably used in accordance with the invention. Alkyl glycosides in which the residue (-glyc) is derived from glucose are particularly preferred. Glucose, maltose, starch and other oligomers of glucose are correspondingly used as starting materials for these compounds which are also known as alkyl glucosides.

In the preparation described above, the alkyl or alkenyl moiety R is derived from long-chain, optionally olefinically unsaturated, primary alcohols which may be branched, but which are preferably not branched. Examples are the synthetic $C_9$-$C_{15}$ oxoalcohols and the $C_8$-$C_{22}$ fatty alcohols obtained from natural fatty acids. $C_8$-$C_{18}$ fatty alcohols and $C_9$-$C_{15}$ oxoalcohols are particularly preferred.

In plant protection in accordance with the present invention, the alkyl glycosides are generally used in the form of blended preparations containing the alkyl glycosides and, optionally, other active substances and auxiliaries. Before application, these preparations are generally diluted to the in-use concentration, although it is also possible in individual cases to prepare the preparations in the in-use concentration from the outset. Typical dilution ratios are from 1:1 to 1:100 and more especially from 1:5 to 1:50.

The alkyl glycosides are preferably formulated as solutions, water preferably being used as solvent, particularly in instances where the alkyl glycosides are used as the sole active substance.

In addition to solutions, however, other formulations typical of plant protection agents, such as for example emulsions, emulsion concentrates, suspensions, pastes, powders or granulates, can also be used for the preparations depending on the particular field of application. Formulations such as these are particularly important in instances where the alkyl glycosides are used in combination with agricultural chemicals which are not formulated as aqueous solutions. In many cases, the surfactant property of certain alkyl glycosides can be additionally used here to stabilize emulsions or suspensions.

The alkyl glycoside content of the preparations can be 100% by weight although, in general, their content is not more than 90% by weight, and preferably not more than 70% by weight, because of the presence of auxiliaries and/or other active substances. In the case of aqueous solutions, the alkyl glycoside content is generally not more than 80% by weight and preferably not more than 70% by weight. The lower limits for preparations used without further dilution are 0.02 to 2% by weight, and preferably 0.1 to 1% by weight. In preparations which are diluted before use, the content is generally more than 3% by weight, preferably more than 5% by weight and more preferably greater than 20% by weight.

Auxiliaries suitable for use in the formulation of the alkyl-glycoside-containing preparations are any of the auxiliaries typically used in plant protection agents providing they are compatible with the alkyl glycosides. Auxiliaries such as these are, for example, organic solvents, solid insoluble carriers, dispersants, emulsifiers, viscosity regulators and diluents.

The in-use concentration of the alkyl glycosides may be varied within wide limits, depending on the application envisaged for the preparations.

In the control of plant pests, the lower limit is generally reached when, with complete wetting of the plants, the alkyl glycosides are applied in just that quantity which is required for the intended effect. As stated above, and depending on the particular pests to be controlled, the lower limit is at 0.02 to 2% by weight and more especially at 0.1 to 1% by weight, although for some applications it may even be distinctly above or below these values. The upper limit to the in-use concentration is largely determined by the solubility of the alkyl glycosides and the viscosity of the solutions. In many cases, aqueous solutions containing 70% by weight alkyl glycoside may still be conveniently prepared and handled. This is of particular significance for large-scale applications where considerable emphasis is placed on saving weight.

The invention will be illustrated but not limited by the following examples.

EXAMPLES

1. Preparation of alkyl glycosides corresponding to formula II (Table 1)

The alkyl glycosides A–D, F and G were prepared by acid-catalyzed reaction of glucose with $C_8$-$C_{18}$ fatty alcohols in accordance with U.S. Pat. No. 3,839,318 (method 1). The alkyl glucosides E and H were prepared from butyl glucoside by transglycosidation in accordance with U.S. Pat. No. 3,547,828 (method 2). With the exception of H, which was first further purified by recrystallization from acetone, all the products were used in technical purity for the production of the preparations of the invention.

The composition and analytical data of the products are shown in Table 1.

TABLE 1

| | Alkyl glucosides A–H | | | |
|---|---|---|---|---|
| Code | R | Method of preparation | n* | OH number |
| A | n-alkyl $C_8$-$C_{10}$ | 1 | 1.8 | 777 |
| B | n-alkyl $C_8$-$C_{10}$ | 1 | 1.3 | 722 |
| C | n-alkyl $C_{12}$-$C_{14}$ | 1 | 1.4 | 661 |
| D | n-alkyl $C_{12}$-$C_{14}$ | 1 | 2.2 | 676 |
| E | tallow alkyl ($C_{16}$-$C_{18}$, partially unsaturated) | 2 | 5.4 | 804 |
| F | n-alkyl $C_8$-$C_{10}$ | 1 | 1 | 709 |
| G | n-alkyl $C_{12}$-$C_{14}$ | 1 | 1 | 590 |
| H | n-alkyl $C_{12}$ | 2 | 1 | 638 |

*According to $^1$H-NMR and the result of hydrolysis

2. Preparation of alkyl glycosides corresponding to formula I

The ethoxylated alkyl glucosides I and K were prepared in accordance with U.S. Pat. No. 2,407,002 by base-catalyzed addition of stoichiometric quantities of ethylene oxide onto the alkyl glucoside G. The crude products were brown, viscous masses and were bleached by addition of 1% $H_2O_2$ (70% solution) and heating to 100° C. before they were used for production of the preparations.

The data for the two compounds were as follows:

| Code | R | n | m | OH number |
|---|---|---|---|---|
| I | n-alkyl $C_{12}$-$C_{14}$ | 1 | 2 | 507 |
| K | n-alkyl $C_{12}$-$C_{14}$ | 1 | 5 | 413 |

3. Production of the plant protection preparations

Preparations in the form of aqueous or aqueous-isopropanolic solutions were prepared from compounds A to K and were used either undiluted or diluted with water

| Code | Active Substance | Concentration % by weight | Solvent |
|---|---|---|---|
| A 30 | A | 30 | water |
| B 60 | B | 60 | water |
| C 2 | C | 2 | water |
| D 6 | D | 6 | water |
| E 10 | E | 10 | water |
| F 40 | F | 40 | water |
| G 4 | G | 4 | water |
| H 2 | H | 2 | water |
| I 10 | I | 10 | water/isopropanol(85:15) |
| K 25 | K | 25 | water/isopropanol(85:15) |

4. Use against aphids

To test the control of aphids, young solanum plants were infected with aphids (*Myzodes persicae*). After an infestation of 100 to 150 aphids was present on the plants, the plants were completely wetted with the above solutions. Five plants were used for each series of tests. The controls were performed 1, 3 and 7 days after the treatment, as indicated in Table 2. The performance of the preparations was calculated as efficiency in accordance with the Abbott formula $$\text{Eff. in \%} = \frac{\text{living in the control} - \text{living in the test}}{\text{living in the control}} \times 100$$

5. Use against spider mites

Dwarf beans were used for the tests for controlling spider mites and were infected with spider mites (*Tetranychus urticae*). After an infestation of from 10 to 15 spider mites per 10 cm² leaf area had been establised, the plants were completely wetted with the solutions (5 plants were used per each series of tests). The controls of the plants were performed 3, 7 and 14 days after the treatment, as indicated in Table 2. The efficiency of the test products was calculated in accordance with the Henderson/Tilton formula:

$$\text{Eff. in \%} = \left(1 - \frac{Bn \times Uv}{Bv \times Un}\right) \times 100$$

$Bn$ = number of mites per 10 cm² on the treated plants afterwards $Uv$ = number of mites per 10 cm² on the untreated plants beforehand $Bv$ = number of mites per 10 cm² on the treated plants beforehand $Un$ = number of mites per 10 cm² on the untreated plants afterwards

TABLE 2

| | | | Use against aphids and spider mites | | | | | |
| | | In-use concentration of the active substance | Aphids Eff. in % after days | | | Spider mites Eff. in % after days | | |
| Preparation | Active substance | % by weight | 1 | 3 | 7 | 3 | 7 | 14 |
|---|---|---|---|---|---|---|---|---|
| A 30 | A | 2.0 | 97.9 | 98.6 | 85.5 | 75.7 | 95.8 | 96.8 |
| B 60 | B | 2.0 | 96.8 | 97.5 | 96.1 | 63.7 | 100 | — |
| B 60 | B | 0.2 | — | — | — | 49.9 | 89.8 | — |
| C 2 | C | 0.2 | 98.4 | 91.4 | 73.9 | — | — | — |
| D 6 | D | 0.2 | 91.4 | 58.0 | 45.1 | — | — | — |
| E 10 | E | 2.0 | 92.2 | — | — | — | — | — |

6. Use against powdery mildew

The preparations were tested against powdery mildew on Elatior Begonias (young plants) which were infected with the pathogen powdery mildew (*Oidium begonia*). The degree of infestation before and after application of the solutions was determined on a scale of 1 to 9 in accordance with the following Table: Effect of the preparation on the infestation:

| | |
|---|---|
| 1 = no infestation | |
| 2 = very slight infestation | up to 2.5% |
| 3 = slight infestation | 2.5 to 5.0% |
| 4 = still slight infestation | 5.0 to 10.0% |
| 5 = moderate infestation | 10.0 to 15.0% |
| 6 = heavy infestation | 15.0 to 25.0% |
| 7 = very heavy infestation | 25.0 to 35.0% |
| 8 = very heavy infestation | 35.0 to 67.5% |
| 9 = total infestation | 67.5 to 100.0% |

Five plants which were infested before the beginning of the test in the series of Table 3 were used for each test solution while uninfested plants were used for the test series of Table 4.

The infested plants were completely wetted by spraying twice at an interval of 14 days and were inspected 7, 14 and 21 days after the first treatment. Table 3 shows the ratings after 21 days and the average of all three ratings.

The uninfested plants were first treated with the test solutions, infected with mildew after drying and treated a second time after 14 days. The effect was evaluated 7, 14 and 21 days after infection. Table 4 shows the results in the form of the ratings after 21 days and the average values of all three ratings.

TABLE 3

Use against powdery mildew
2 treatments at an interval of 14 days,
infestation on a rating scale of 1 to 9

| Code | Active substance | In-use concentration of the active substance % by weight | Beginning of test | End of test | ⌀ of all evaluations |
|---|---|---|---|---|---|
| A 30 | A | 2.0 | 2.6 | 1.2 | 1.5 |
| B 60 | B | 0.2 | 2.2 | 1.6 | 1.9 |
| B 60 | B | 2.0 | 2.4 | 1.8 | 1.8 |
| F 40 | F | 0.2 | 2.4 | 2.5 | 2.4 |
| F 40 | F | 2.0 | 2.4 | 1.6 | 1.5 |
| G 4 | G | 0.2 | 2.4 | 2.2 | 1.9 |
| G 4 | G | 2.0 | 2.6 | 1.0 | 1.5 |
| I 10 | I | 2.0 | 2.8 | 1.2 | 1.5 |
| H 2 | H | 2.0 | 3.0 | 1.0 | 1.8 |
| untreated | | | 2.8 | 5.5 | 5.6 |

TABLE 4

Preventive application:
treatment, infection, second treatment 14 days after the first, infestation on a rating scale of 1 to 9

| Code | Active substance | In-use concentration of the active substance % by weight | Beginning of test | End of test | ⌀ of all controls |
|---|---|---|---|---|---|
| B 60 | B | 0.2 | 1 | 1.8 | 1.2 |
| B 60 | B | 2.0 | 1 | 1.8 | 1.2 |
| F 40 | F | 2.0 | 1 | 2.0 | 1.3 |
| I 10 | I | 2.0 | 1 | 1.4 | 1.3 |
| K 25 | K | 0.2 | 1 | 1.2 | 1.1 |
| K 25 | K | 2.0 | 1 | 1.2 | 1.1 |
| H 2 | H | 2.0 | 1 | 1.6 | 1.1 |
| untreated | | | | 3.8 | 3.2 |

We claim:

1. A method for treating plants to control plant pests comprising applying to the locus of the pest a pest controlling quantity of a wax free composition containing at least one alkyl glycoside having the formula $$(H(\text{-glyc})_n R)(EO)_m \qquad (I)$$

wherein (-glyc) is the residue of a monosaccharide, n is a number of from 1 to 6, R is a primary $C_8$–$C_{22}$ alkyl or alkenyl group attached to the (-glyc) group by a glycoside bond, EO is the ethyleneoxy group, and m is a number of from 0 to 100.

2. The method of claim 1 wherein the plants being treated are crop or ornamental plants.

3. The method of claim 1 wherein the plant pest being controlled is an insect.

4. The method of claim 1 wherein the plant pest being controlled is a mite.

5. The method of claim 1 wherein the plant pest being controlled is a fungi.

6. The method of claim 1 wherein the residue (-glyc) in formula I is a residue from glucose.

7. The method of claim 1 wherein n in formula I has a value of from 1 to 3.

8. The method of claim 1 wherein R in formula I contains from 8 to 18 carbon atoms.

9. The method of claim 1, wherein in formula I m is a number from 0 to 10.

10. The method of claim 9 wherein m=0.

11. The method of claim 1 wherein the organism controlling quantity of alkyl glycoside is an aqueous solution thereof having an alkyl glycoside content of from about 0.02 to about 90% by weight.

12. The method of claim 11 wherein said content is from about 0.1 to about 70% by weight.

13. The method of claim 11 wherein said content is from about 3 to about 70% by weight.

14. The method of claim 1 wherein the alkyl glycoside is the only plant pest controlling material employed.

15. The method of claim 1 wherein the plant pest being controlled is insects the residue (-glyc) in formula I is a residue from glucose, n has a value of from 1 to 3, R contains from 8 to 18 carbon atoms, and m is a number from 0 to 10.

16. The method of claim 1 wherein the plant pest being controlled is mites, the residue (-glyc) is a residue from glucose, n has a value of from 1 to 3, R contains from 8 to 18 carbon atoms, and m is a number from 0 to 10.

17. The method of claim 1 wherein the plant pest being controlled is fungi, the residue (-glyc) is a residue from glucose, n has a value of from 1 to 3, R contains from 8 to 18 carbon atoms, and m is a number from 0 to 10.

18. A method for treating plants to control plant pests comprising applying to the locus of the plant pests a pest controlling quantity of a wax free composition comprising at least one alkyl glycoside of the formula $$(H(\text{-glyc})_n R)(EO)_m \qquad (I)$$

wherein (-glyc) is the residue of a monosaccharide, n is a number of from 1 to 6, R is a primary $C_8$–$C_{22}$ alkyl or alkenyl group attached to the (-glyc) group by a glycoside bond, (EO) is the ethylenoxy group, and m is a number of from 0 to 100 and at least one member selected from the group consisting of insecticides, fungicides, acaricides and herbicides.

* * * * *